United States Patent
Shvetsov et al.

(10) Patent No.: US 9,289,261 B2
(45) Date of Patent: Mar. 22, 2016

(54) ELECTROSURGICAL DEVICE WITH VACUUM PORT

(75) Inventors: Kyrylo Shvetsov, Tonawanda, NY (US); Anthony L Lizauckas, III, Williamsville, NY (US); Gregory J. Pepe, Lancaster, NY (US); Daniel R Palmerton, Elma, NY (US); Joseph J Lynch, Williamsville, NY (US); Christopher A Palmerton, Clarence, NY (US)

(73) Assignee: Buffalo Filter LLC, Lancaster, NY (US)

( * ) Notice: Subject to any disclaimer, the term of this patent is extended or adjusted under 35 U.S.C. 154(b) by 1349 days.

(21) Appl. No.: 13/021,494

(22) Filed: Feb. 4, 2011

(65) Prior Publication Data

US 2011/0190768 A1    Aug. 4, 2011

Related U.S. Application Data

(60) Provisional application No. 61/301,328, filed on Feb. 4, 2010, provisional application No. 61/318,023, filed on Mar. 26, 2010.

(51) Int. Cl.
*A61B 18/14*      (2006.01)
*A61B 18/18*      (2006.01)

(52) U.S. Cl.
CPC ..................... *A61B 18/18* (2013.01)

(58) Field of Classification Search
CPC ................... A61B 2218/007; A61B 2218/008; A61B 18/082; A61B 18/1477; A61B 2018/00577; A61B 2018/00625
USPC .................................................. 606/45–50
See application file for complete search history.

(56) References Cited

U.S. PATENT DOCUMENTS

| | | | | |
|---|---|---|---|---|
| 3,825,004 | A | * | 7/1974 | Durden, III ..................... 604/20 |
| 5,085,657 | A | * | 2/1992 | Ben-Simhon ................... 606/42 |
| 5,192,267 | A | * | 3/1993 | Shapira et al. .................. 604/22 |
| 5,234,428 | A | * | 8/1993 | Kaufman ........................ 606/45 |
| 5,318,565 | A | * | 6/1994 | Kuriloff et al. ................. 606/49 |
| 5,413,575 | A | * | 5/1995 | Haenggi .......................... 606/45 |
| 5,709,675 | A | * | 1/1998 | Williams ......................... 606/1 |
| 6,146,353 | A | * | 11/2000 | Platt, Jr. .......................... 604/22 |
| 6,635,034 | B1 | * | 10/2003 | Cosmescu ..................... 604/289 |
| 6,733,495 | B1 | * | 5/2004 | Bek et al. ........................ 606/34 |
| 2006/0264928 | A1 | * | 11/2006 | Kornerup et al. ............... 606/45 |
| 2009/0018539 | A1 | * | 1/2009 | Cosmescu ....................... 606/41 |
| 2009/0062791 | A1 | * | 3/2009 | Lee et al. ........................ 606/45 |
| 2010/0145333 | A1 | * | 6/2010 | Dethier et al. .................. 606/42 |

* cited by examiner

*Primary Examiner* — Michael Peffley
(74) *Attorney, Agent, or Firm* — Phillips Lytle LLP (57) ABSTRACT

An electrosurgical device comprising: an electrode having a first portion whose exterior is electrically uninsulated, a second portion whose exterior is electrically insulated, and a third portion; an elongated hollow body having an internal cavity, a front end, a rear end, an external surface, and an electrical wire arranged within the body. The hollow body is configured to reversibly receive the third portion of the electrode at the front end of the body such that electrical contact is made between the electrode and the electrical wire and the second portion of the electrode is not surrounded by the hollow body. A first button is provided for controlling a current flow at a first level to the electrode and is arranged on the external surface. A vacuum tube is slidably engaged by the body and has an inlet generally facing the front end and adjacent the electrode. A vacuum outlet port is arranged near the rear end of the body, and the outlet port, internal cavity, and vacuum inlet are in fluid communication with each other.

29 Claims, 6 Drawing Sheets

ELECTROSURGICAL DEVICE WITH VACUUM PORT

CROSS-REFERENCE TO RELATED APPLICATIONS

The present application claims the benefit of U.S. Provisional Application No. 61/301,328, filed Feb. 4, 2010, and U.S. Provisional Application No. 61/318,023, filed Mar. 26, 2010, each of which is hereby incorporated by reference.

FEDERALLY SPONSORED RESEARCH

Not applicable.

TECHNICAL FIELD

The present invention relates generally to smoke evacuation and, more specifically, to an electrosurgical device with smoke evacuation during medical procedures.

BACKGROUND

Surgical smoke and aerosol, or plume, is created in connection with surgery. For example, when laser or electrosurgical energy is delivered to a cell, heat is created. This heat vaporizes the intracellular fluid, which increases the pressure inside the cell and eventually causes the cell membrane to burst. In this example, a plume of smoke containing water vapor is released into the atmosphere of the operating room or doctor's office. At the same time, the heat created may char the protein and other organic matter within the cell, and may cause thermal necrosis in adjacent cells. The charring of cells may also release other harmful contaminants, such as carbonized cell fragments and gaseous hydrocarbons.

BRIEF SUMMARY OF THE INVENTION

With parenthetical reference to the corresponding parts portions or surfaces of the disclosed embodiments, merely for the purposes of illustration and not by way of limitation, the present embodiment provides an electrosurgical device comprising: an electrode (11) having a first portion (12) whose exterior is electrically uninsulated, a second portion (13) whose exterior is electrically insulated, and a third portion (14); an elongated hollow body (22) having an internal cavity (26), a front end (28), a rear end (29), an external surface (17), and an electrical wire (27) arranged within the body and the hollow body configured to reversibly receive the third portion of the electrode at the front end of the body such that electrical contact is made between the electrode and the electrical wire, and where the second portion of the electrode is not surrounded by the hollow body. A first button (18) is arranged on the body's external surface for controlling a current flow at a first level. A vacuum tube (16) is slidably engaged by the body and has an inlet (15) generally facing the front end of the body, and the vacuum tube is arranged adjacent the electrode. A vacuum outlet port (24) is arranged near the rear end, and the outlet port, internal cavity, and vacuum inlet are in fluid communication with each other.

The body may be ergonometrically shaped to be received by a user's hand. The inlet may be shaped to face away from the electrode. The body may be pencil shaped and may contain friction striations (21). The friction striations may be curved. The electrode may be monopolar, bipolar, or sesquipolar.

The device may have a second button (19) for controlling a current flow at a second level to the electrode, and may have a third button (73) to control the vacuum source.

The device may also have: a light source (71) arranged to illuminate an area near the electrode, a battery (72) for providing power to the light source, a button (78) for controlling the illumination light, a swivel joint (74) between the body and the outlet port, and the electrical line (35, 85) may pass through the swivel joint.

A filter (75) may be arranged within the internal cavity and the filter may have an RFID tag (76) containing filter information. The vacuum inlet may have a substantially rectangular cross section.

In another form, the electrosurgical device comprises: an electrode; an elongated hollow body having an internal cavity, a front end, a rear end, an external surface, and an electrical wire arranged within the body, in which the hollow body is configured to reversibly receive the electrode; the hollow body is shaped to have an ergonometric orientation complementary to a user's hand; a first button for controlling a current flow at a first level to the electrode and arranged on the external surface; a vacuum tube slidably engaged by the body and having an inlet generally facing the front end and directed away from the electrode, the vacuum tube arranged above the electrode. A vacuum outlet port (24, 34, 84) is arranged near the rear end of the body and the outlet port, internal cavity, and vacuum inlet are in fluid communication with each other.

The device may be configured to have an electrically insulated portion not surrounded by the body when the electrode is received by the body. The body may be pencil shaped and may contain friction striations and the striations may be curved. The electrode may be monopolar, bipolar, or sesquipolar.

The device may have a second button for controlling a current flow at a second level to said electrode or a third button for controlling a vacuum source. The inlet may have a substantially rectangular cross section. The device may also have a light source arranged to illuminate an area near the electrode; a battery for providing power to the light source; a button for controlling the illumination light; and a swivel joint between the body and the outlet port. The electrical line may pass through said swivel joint.

The device may contain a filter arranged within the internal cavity and may contain an RFID tag containing filter information.

In another form, an electrosurgical device is provided comprising: an electrode; an elongated hollow body having an internal cavity, a front end, a rear end, an external surface, and an electrical wire arranged within the body, a hollow body is configured to reversibly receive the electrode, in which the hollow body is shaped to have an ergonometric orientation complementary to a user's hand; a first button for controlling a current flow at a first level to the electrode and arranged on the external surface; a vacuum tube engaged by the body and having an inlet generally facing the front end, the vacuum tube arranged adjacent the electrode and the inlet having a substantially vertical cross section when the device is held in the ergonometric orientation. A vacuum outlet port may be arranged near the rear end, and the outlet port, internal cavity, and vacuum inlet are in fluid communication with each other.

The device has means for preventing the vacuum tube from obstructing a user's view of said electrode and means for removing the electrode without electrically contacting the electrode. The means for preventing the vacuum tube from obstructing a user's view may comprise a slidable engagement between the vacuum tube and the body. The means for preventing the vacuum tube from obstructing a user's view comprises an inlet shaped to have a cross section perpendicular to a user's line of sight towards the electrode when using the device. The means for removing the electrode without electrically contracting the electrode may comprise an insulation coating on the electrode which remains accessible to a user's hand when the electrode is received by the body.

The device inlet may have a substantially rectangular cross section. The means for preventing the vacuum tube from obstructing a user's view may comprise a vacuum tube made of clear material.

DETAILED DESCRIPTION OF THE PREFERRED EMBODIMENTS

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Structure:

Referring now to the drawings, the present invention broadly provides an electrosurgical device having a vacuum port, generally indicated at 10, which is particularly adapted for (but is not limited to) suctioning smoke during electrosurgery.

Figure 1:
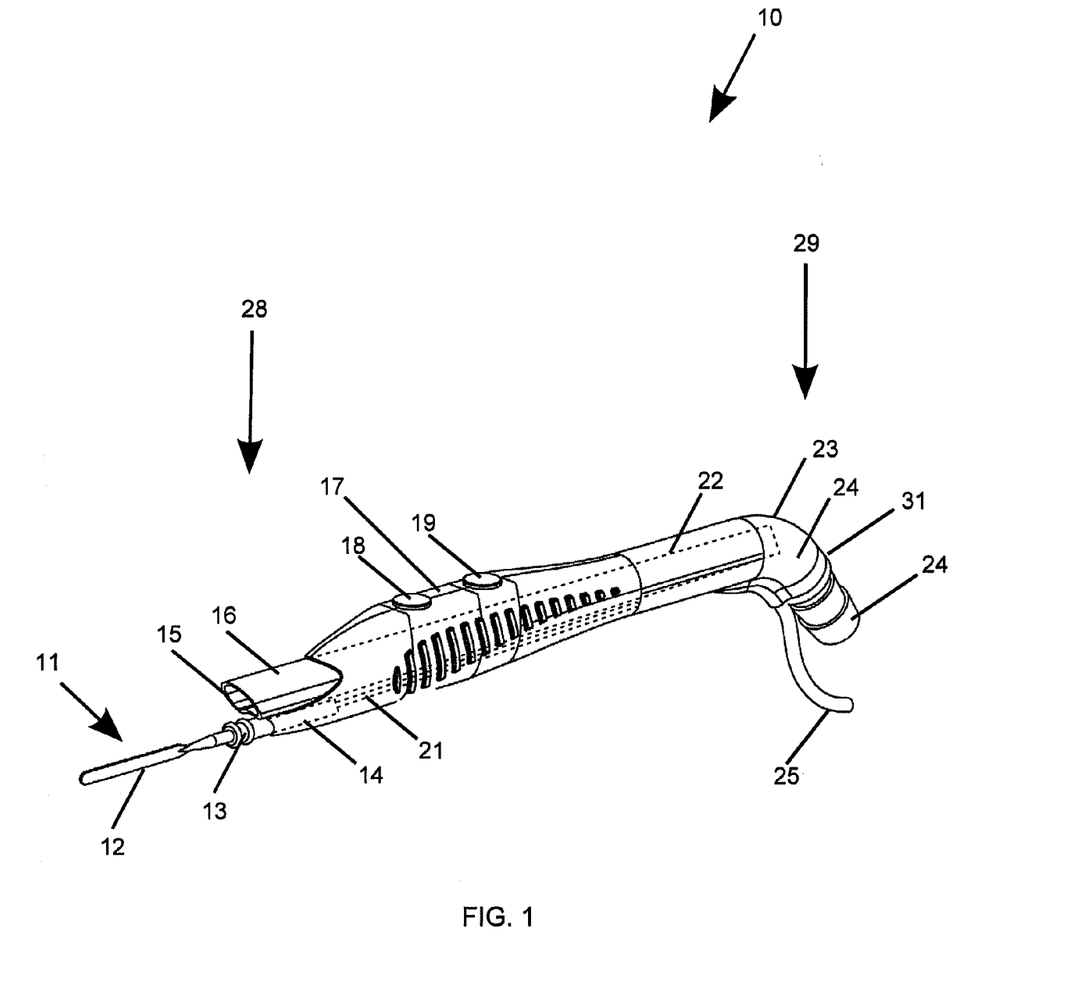
FIG. 1 is a perspective view showing a first embodiment of the electrosurgical device in a vacuum tube retracted configuration.
Figure 2:
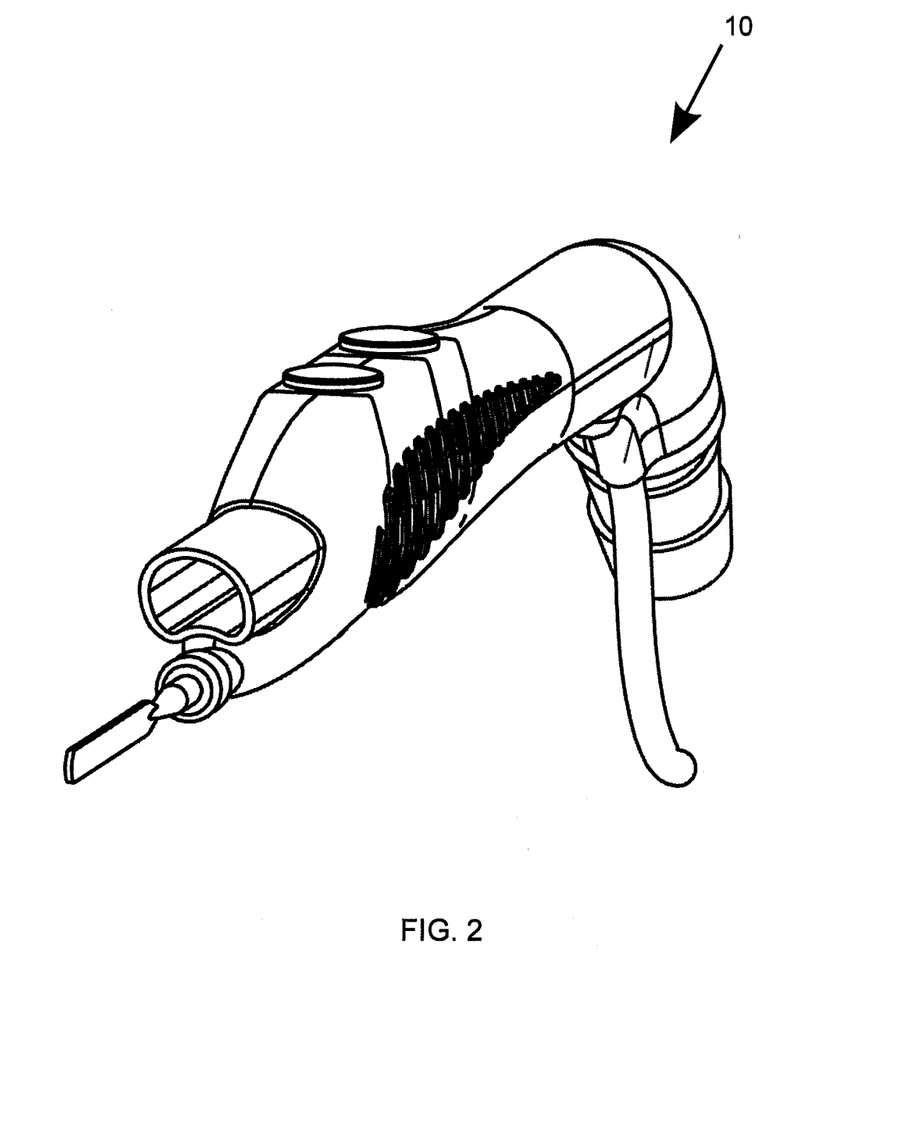
FIG. 2 is a perspective view of the first embodiment in a vacuum tube retracted configuration.

In FIG. 1, the electrosurgical device is shown as broadly including hollow body 22 with front end 28 holding electrode 11, rear end 29 holding vacuum port 24, electrical line 25, coagulate button 18, cut button 19, and vacuum tube 16. Vacuum tube 16 is slidably engaged by hollow body 22 and is shown in the refracted configuration in FIG. 1.

Electrode 11 has uninsulated portion 12, connected to insulated portion 13, which is connected to third portion 14. As shown in FIG. 1, insulated portion 13 contains circular friction ridges. Electrode third portion 14 is reversibly and compressively engaged by hollow body 22. When engaged by hollow body 22, electrode 11 makes electrical contact with internal wire 27, which is connected to electrical line 25 through buttons 18 and 19 within elongated body 22. When electrode 11 is engaged to body 22, portion 13 of electrode 11 is not encircled by body 22 and can be easily gripped by a user's fingers.

Electrical line 25 within elongated body 22 extends from buttons 18 and 19 to the rear of body 22. At the rear of body 22 electrical line 25 exits body 22 adjacent to vacuum exit port 24.

Vacuum tube 16 has an inlet facing generally towards the front end of body 22. In embodiment 10, inlet 15 is also angled downwards towards electrode 11, and is crescent shaped as shown in FIG. 1. However, in other embodiments, the cross section of inlet 15 is angled upwards away from electgrod 11, and is generally rectangular shaped. Hollow cavity 26 of body 22 extends from front end 28 to rear end 29. Vacuum tube 16 is compressively engaged by the front end of hollow cavity 26. Vacuum tube 16 is capable of telescopically extending from and retracting into cavity 26. However, even when fully retracted, a portion of vacuum tube 16 will be protruding from body 22 and can be laterally gripped by a user.

Vacuum tube 16 is in fluid communication with hollow cavity 26, and vacuum exit port 24. Elongated body 22 contains bend 23 in its body near vacuum port 24 as shown in FIG. 1. The interface between bend 23 and vacuum exit port 24 forms a swivel joint.

On the exterior lateral surfaces of body 22 are curved friction ridges 21. On top surface 17 of body 22 is cut button 18 and coagulate button 19.

Vacuum tube 16 is made of clear plastic. The colors of buttons 18 and 19, body 22, and electrode insulated portion 14 are all distinct. Electrical line 25 is flexible.

Figure 3:
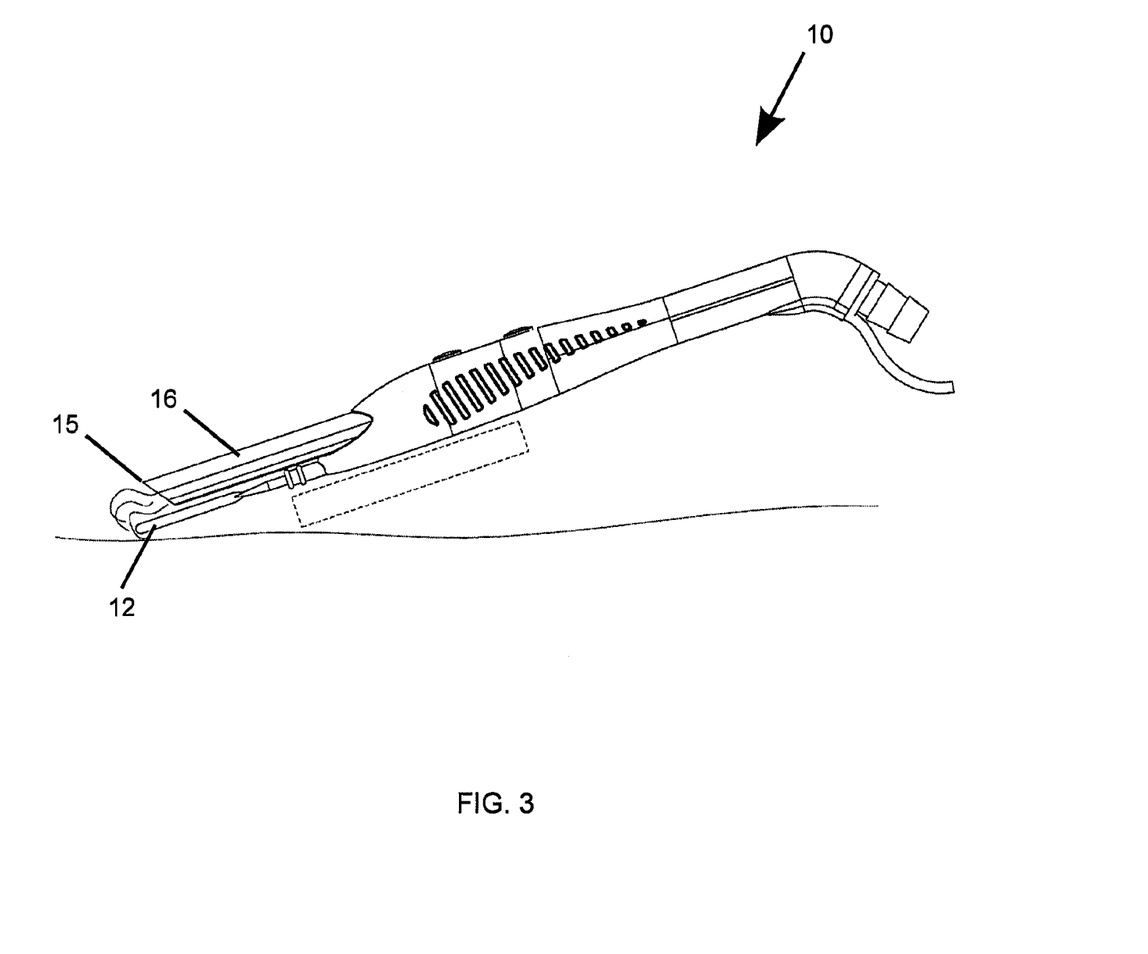
FIG. 3 is a side view of the first embodiment in a vacuum tube extended configuration.

FIG. 3 shows first embodiment 10 with vacuum tube 16 in the extended configuration. In the extended configuration, inlet 15 is positioned closer to electrode portion 12.

Operation

A user initially prepares first embodiment 10 by inserting electrode 11 into front end 28 of elongated body 22. By holding electrode 11 by insulated portion 13, the circular ridges along insulated portion 12 provide increased friction and grip for inserting electrode 11 into body 22. Electrode 11 is firmly pressed into body 22 such that electrode 11 makes electrical contact with internal wire 27 within body 22. Since insulated portion 13 extends outside body 22 when electrode 11 is fully inserted, the user is able to insert the electrode without ever touching uninsulated portion 12 of electrode 11.

The user next adjusts vacuum tube 16 to the proper extension distance. Access to the lateral edges of vacuum tube 16 is not hindered by body 22 and the user can easily grip vacuum tube 16 by the lateral edges and telescopically adjust vacuum tube 16 to an appropriate extension amount.

An external vacuum tube is connected to outlet port 24, insuring that outlet port 24 is securely inserted such that an air-tight seal is formed. The opposing end of the external vacuum tube is connected to a vacuum source, and electrical line 25 is connected to an electrosurgical RF power source.

In preparation for electrosurgery, the user will grip body 22 similar to holding a pencil, and the user's thumb and non-index fingers will be placed on opposite sides of body 22 along finger friction ridges 21. As shown in FIG. 3, the shape of the device is ergonometrically suited to a user's hand. When the user is ready to initiate electrosurgery, either button 18, for cutting, or button 19, for coagulating, will be depressed by the user's index finger. Pressing button 18 will cause current to pass from electrical line 25 to internal wire 27 and out electrode 12 to a patient's body with enough current to typically cause cutting of tissue. The electrical current through the tissue causes intense heat and smoke to form.

As shown in FIG. 3, the smoke produced during electrosurgery is suctioned by vacuum tube 16. During surgery, the user may easily adjust vacuum tube 16's position, either extending it closer to electrode portion 12 in order better capture smoke, or retracting it closer towards body 22 in order to provide the user with a less obstructed view of the surgical area.

The current flow and vacuum process is similar if the user uses coagulate button 19 instead of cut button 18. However, the current level for coagulate will be less than for cutting.

Since vacuum tube 16 is arranged above electrode portion 13, it is in a good position to capture smoke which typically travels upwards from the treatment region due to convection. In the position above the electrode, vacuum tube 16 is more likely to capture smoke than if it were arranged under electrode 13. Additionally, since vacuum tube is not on the bottom side of body 22, there is decreased risk of vacuum inlet 15 coming into contact with the patient's body which could cause trauma.

During the surgery, whenever the user's hand and carrying with it the elongated body along the body's longitudinal axis, the swivel between bend 23 and outlet port 24 allows torsional strain to be released.

If during the surgery a different electrode style is needed, the user may easily pull electrode 11 off of body 22. Since insulated portion 13 of electrode 11 is easily accessible to the user's fingers, the user may easily remove electrode 11 without touching electrically uninsulated areas of the electrode. This is an added safety feature to help prevent the user from being burned from accidental activation of the electrosurgical device during changing of the electrode. The circular friction ridges along insulated portion 13 and friction ridges 21 along elongated body 22 also help to provide increased stability during the process of removing and inserting electrodes.

Other Embodiments

Figure 4:
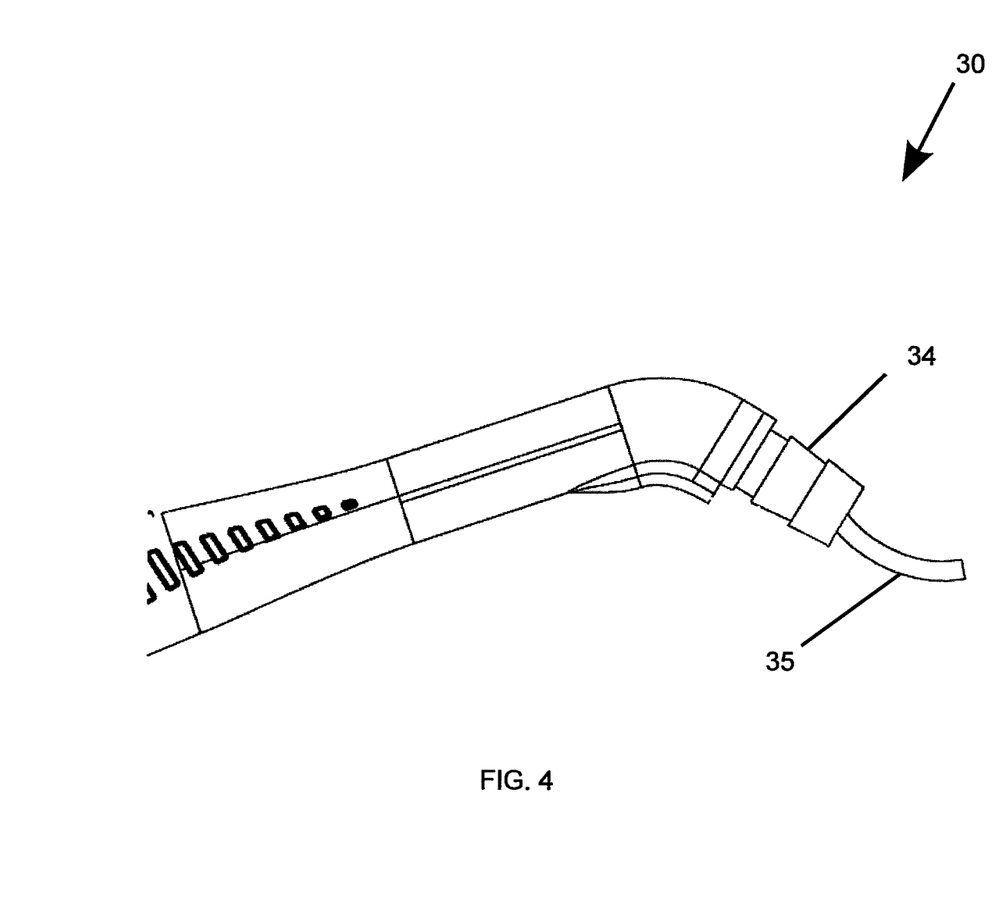
FIG. 4 is a side view of the rear end of a second embodiment of the electrosurgical device having the electrical line passing through the outlet port.

FIG. 4 discloses second embodiment 30 of an electrosurgical device in which electrical line 35 passes through the center of outlet port 34. By passing through outlet port 34, electric line 35 will not wrap around the external vacuum tube when the device is twisted relative to the external vacuum tube. This reduces the chance of discomfort for the user by minimizing rotational strains on the user's movement.

Figure 5:
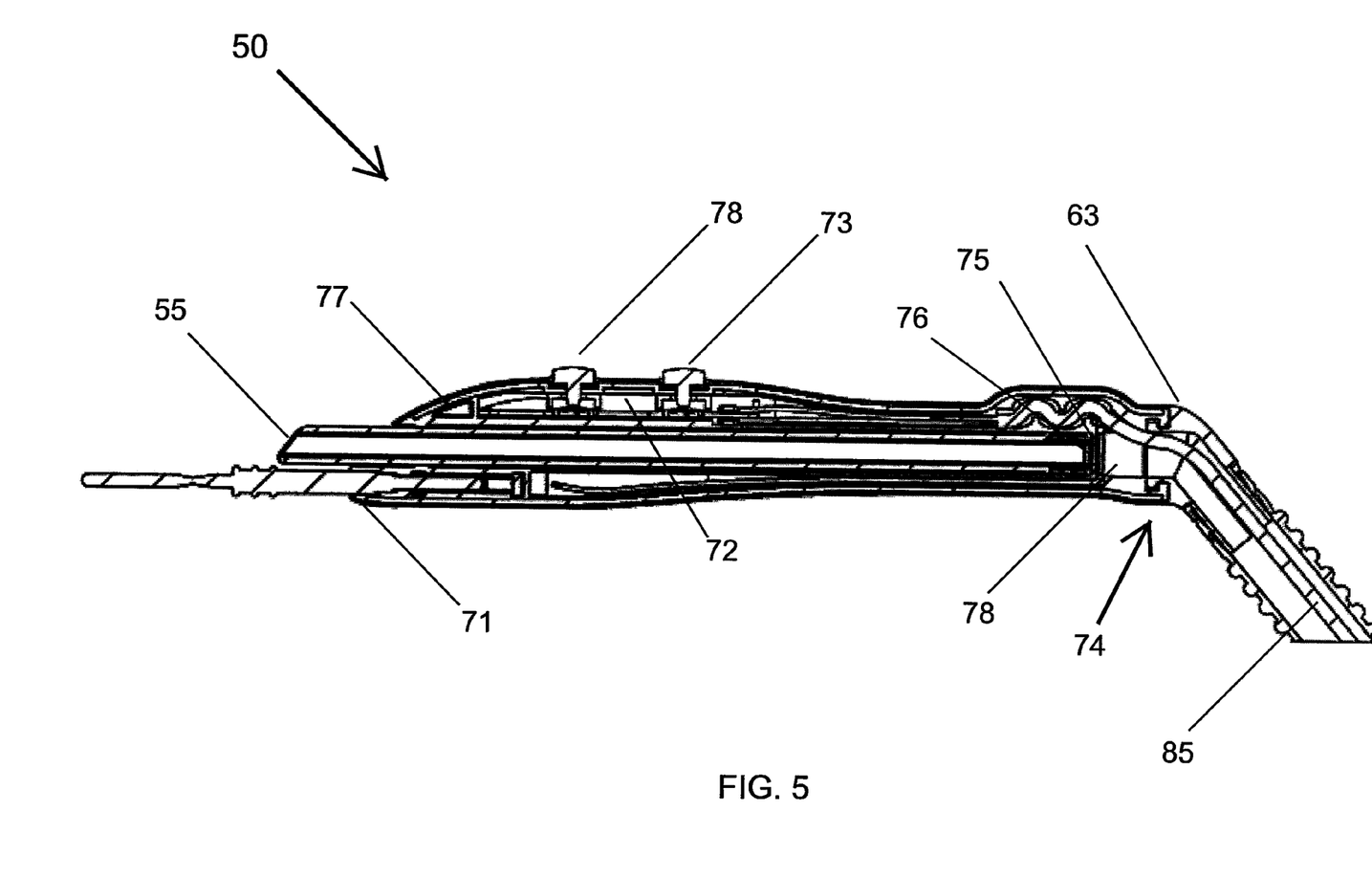
FIG. 5 is a section view of a third embodiment.

FIG. 5 shows a sectional view of third embodiment 50 of an electrosurgical device. As shown, vacuum inlet 55 is angled upwards, away from the electrode, such that when the device is held correctly during surgery, the cross section of the nozzle will be generally vertical and parallel to the user's line of sight as the user looks at the treatment area. In this arrangement, vacuum inlet 55 can be placed as close as possible to the treatment area without obstructing the user's view. For example, in this configuration, both the top of the nozzle and the bottom of the nozzle are flush with the user's line of sight, as close as possible to the smoke creation region before starting to obstructing the user's view. This is in contrast with first embodiment 10 in which when the top of the nozzle is up against the user's line of sight, the bottom of the nozzle is retracted from the smoke creation region.

Figure 6:
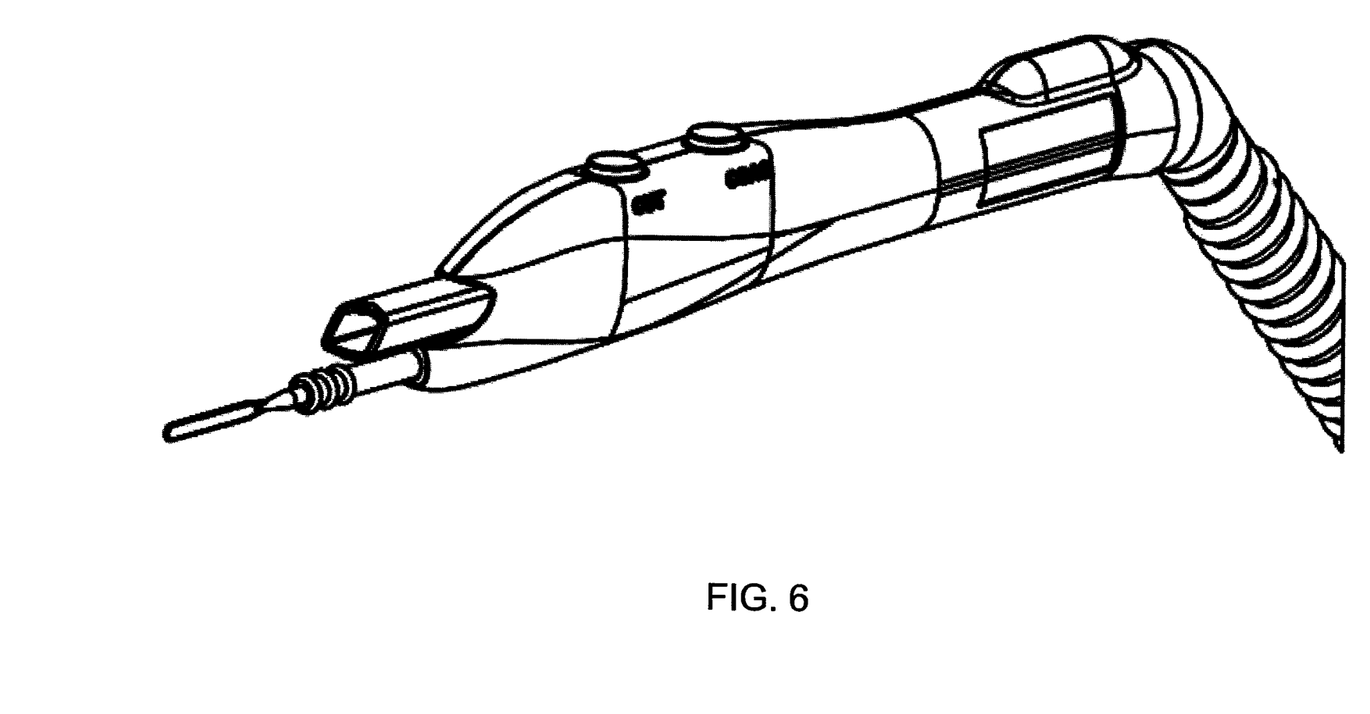
FIG. 6 is a perspective view of a fourth embodiment.

Additionally, as shown in FIG. 6, vacuum tube 56 has a generally rectangular shaped cross section. While the crescent shaped cross section of first embodiment 10 allows the vacuum tube to enclose the electrode to increase the chances of sucking up the created smoke, a rectangular cross section allows for the complete electrosurgical device to have a shorter vertical profile. The shorter vertical profile makes the electrosurgical device easier to handle.

Also embodiment 50 contains illumination light 71, light toggle button 78, and light battery 72 for providing greater illumination of the surgical region. Swivel joint 74 is arranged on the front facing side of bend 63. Embodiment 50 further contains filter 75 within hollow cavity 66. Filter 75 helps remove particulate matter, moisture, and odor from the smoke plume suctioned. The filter contains RFID tag 76 which contains filter information as well as provides a tracking ID for the electrosurgical device. Also, vacuum control button 73 allows the vacuum source to be switched on and off manually directly on the electrosurgical device. RFID sensor 77, which is electrically isolated from the electrosurgical power source, is connected to a remote vacuum source controller which is configured to automatically turn the vacuum source on when sensor 77 detects RF energy from either the cut of coagulate modes.

Advantages

The embodiments disclosed resulted in a number of unexpected results. By arranging the vacuum tubes above the electrode instead of below the electrode a greater portion of the smoke plume was able to be captured. Additionally, by no longer having the vacuum tube on the bottom of the electrosurgical device, the chances of injuring the patient from trauma cause by accidentally bringing the vacuum inlet nozzle onto the patient's exposed surgical site is reduced.

The user's view of the surgical site was surprisingly greatly improved by using a clear vacuum tube. Since light can easily pass through the vacuum tube, reduced amount of shadows are cast on the surgical site. Additionally, since the vacuum tube level of extension can be telescopically adjusted, an optical configuration is obtained for user's of different heights or styles of holding the electrosurgical device. Further, since not all electrodes are the same length, the vacuum tube extension can be adjusted to match the particular electrode used. The upward angled configuration of the vacuum inlet is also particularly advantageous in that it allows the suction source to get as close to the smoke generation region as possible without obstructing the user's view.

By designing the electrosurgical device such that an insulated portion of the electrode is available to be grabbed when the electrode is fully inserted, the insertion and removal of electrodes is made easier and safer. The user is less likely to get accidentally burned when changing the electrode since he/she can grid the electrode on an electrically insulated portion. Further, the use of friction ridges on the insulated portion of the electrode and the elongated body sides, the chance that the device slips in the user's hands is reduced. This is particularly important since the surgical process is likely to cause blood and other slippery body fluids to end up on the device.

The disclosed embodiments also increase surgical efficiency through the illumination offered by an attached light, the reduction of rotational strain by the external vacuum tube swivel and electrical line positioning within the swivel, and the button for controlling the vacuum source. Additionally, the RF sensor within the electrosurgical device allows the vacuum source to be automatically controlled by a circuit which is electrically isolated from the electrosurgical power supply.

Having fully disclosed the preferred form of the electrosurgical device and several variations thereof, persons skilled in the art will readily appreciate that various additional changes may be made without departing from the scope of the invention as set forth in the following claims.

The invention claimed is:

1. An electrosurgical device comprising:
   an electrode having a first portion whose exterior is electrically uninsulated, a second portion whose exterior is electrically insulated, and a third portion;
   an elongated hollow body having an internal cavity, a front end, a rear end, an external surface, and an electrical wire arranged within said body, said hollow body configured to reversibly receive said third portion of said electrode at said front end of said body such that electrical contact is made between said electrode and said electrical wire and said second portion of said electrode is not surrounded by said hollow body;
   a first button for controlling a current flow at a first level to said electrode and arranged on said external surface;
   a vacuum tube slidably engaged by said body and having an inlet generally facing said front end, said vacuum tube arranged adjacent said electrode said vacuum tube arranged above said electrode and facing towards said front end and away from said electrode, wherein the vacuum tube comprises an inlet shaped to have a cross section parallel to a user's line of sight towards said electrode when using said device;
   a vacuum outlet port arranged near said rear end, said outlet port, internal cavity, and vacuum inlet in fluid communication with each other;
   a swivel joint between said body and said outlet port; and
   wherein said electrical line passes through said swivel joint.

2. An electrosurgical device as set forth in claim 1 wherein said body is ergonometrically shaped to be received by a user's hand.

3. An electrosurgical device as set forth in claim 1 wherein said body is pencil shaped.

4. An electrosurgical device as set forth in claim 1 wherein said body contains friction striations.

5. An electrosurgical device as set forth in claim 1 wherein said electrode is monopolar, bipolar, or sesquipolar.

6. An electrosurgical device as set forth in claim 1 and further comprising a second button for controlling a current flow at a second level to said electrode.

7. An electrosurgical device as set forth in claim 6 and further comprising a third button disposed on the body for manually changing the state of an on/off switch connected to a vacuum source.

8. An electrosurgical device as set forth in claim 1 and further comprising:
   a light source arranged to illuminate an area near said electrode;
   a battery for providing power to said light source; and
   a button for controlling said light source.

9. An electrosurgical device as set forth in claim 1 and further comprising a filter arranged within said internal cavity.

10. An electrosurgical device as set forth in claim 9 wherein said filter comprises an RFID tag containing filter information.

11. An electrosurgical device as set forth in claim 1 wherein said inlet has a substantially rectangular cross section.

12. An electrosurgical device as set forth in claim 1, wherein the inlet of the vacuum tube is shaped to have a cross-section disposed at an obtuse angle with respect to a longitudinal axis of the first portion of the electrosurgical device.

13. An electrosurgical device comprising:
    an electrode;
    an elongated hollow body having an internal cavity, a front end, a rear end, an external surface, and an electrical wire arranged within said body, said hollow body configured to reversibly receive said electrode;
    said hollow body shaped to have an ergonometric orientation complementary to a user's hand;
    a first button for controlling a current flow at a first level to said electrode and arranged on said external surface;
    a vacuum tube slidably engaged by said body and having an inlet, said vacuum tube arranged above said electrode and facing towards said front end and away from said electrode wherein the vacuum tube comprises an inlet shaped to have a cross section parallel to a user's line of sight towards said electrode when using said device;
    a vacuum outlet port arranged near said rear end, said outlet port, internal cavity, and vacuum inlet in fluid communication with each other;
    a swivel joint between said body and said outlet port; and
    wherein said electrical wire passes through said swivel joint.

14. An electrosurgical device as set forth in claim 13 wherein said device is configured to have an electrically insulated portion not surrounded by said body when said electrode is received by said body.

15. An electrosurgical device as set forth in claim 13 wherein said body is pencil shaped.

16. An electrosurgical device as set forth in claim 13 wherein said body contains curved friction striations.

17. An electrosurgical device as set forth in claim 13 wherein said electrode is monopolar, bipolar, or sesquipolar.

18. An electrosurgical device as set forth in claim 13 and further comprising a second button for controlling a current flow at a second level to said electrode.

19. An electrosurgical device as set forth in claim 18 and further comprising a third button for controlling a vacuum source.

20. An electrosurgical device as set forth in claim 13 wherein said inlet has a substantially rectangular cross section.

21. An electrosurgical device as set forth in claim 13 and further comprising:
    a light source arranged to illuminate an area near said electrode;
    a battery for providing power to said light source; and
    a button for controlling said light source.

22. An electrosurgical device as set forth in claim 13 and further comprising a filter arranged within said internal cavity.

23. An electrosurgical device as set forth in claim 22 wherein said filter comprises an RFID tag containing filter information.

24. An electrosurgical device comprising:
    an electrode having a first portion whose exterior is electrically uninsulated;
    an elongated hollow body having an internal cavity, a front end, a rear end, an external surface, and an electrical wire arranged within said body, said hollow body configured to reversibly receive said electrode;
    said hollow body shaped to have an ergonometric orientation complementary to a user's hand;
    a first button for controlling a current flow at a first level to said electrode and arranged on said external surface;

a vacuum tube engaged by said body and having an inlet generally facing said front end and away from said electrode, said vacuum tube arranged adjacent said electrode;

a vacuum outlet port arranged near said rear end, said outlet port, internal cavity, and vacuum inlet in fluid communication with each other;

means for preventing said vacuum tube from obstructing a user's view of said electrode, wherein said means for preventing said vacuum tube from obstructing a user's view comprises said vacuum tube arranged above said electrode and facing towards said front end and away from said electrode, and the inlet shaped to have a cross section parallel to a user's line of sight towards said electrode when using said device; and means for removing said electrode without electrically contacting said electrode.

25. An electrosurgical device as set forth in claim 24 wherein said means for preventing said vacuum tube from obstructing a user's view comprises slidable engagement between said vacuum tube and said body.

26. An electrosurgical device as set forth in claim 24 wherein said means for removing said electrode without electrically contracting said electrode comprises an insulation coating on said electrode which remains accessible to a user's hand when said electrode is received by said body.

27. An electrosurgical device as set forth in claim 24 wherein said inlet has a generally rectangular cross section.

28. An electrosurgical device as set forth in claim 24 wherein said means for preventing said vacuum tube from obstructing a user's view comprises a vacuum tube comprising clear material.

29. An electrosurgical device as set forth in claim 24, wherein the inlet of the vacuum tube is shaped to have a cross-section disposed at an obtuse angle with respect to a longitudinal axis of the first portion of the electrosurgical device.

* * * * *